United States Patent
Schulz et al.

(10) Patent No.: US 12,202,787 B2
(45) Date of Patent: Jan. 21, 2025

(54) METHOD AND SYSTEM FOR THE SYNTHESIS OF METHANOL

(71) Applicants: GASCONTEC GMBH, Bad Homburg (DE); THYSSENKRUPP INDUSTRIAL SOLUTIONS AG, Essen (DE)

(72) Inventors: Alexander Schulz, Frankfurt (DE); Beata Banik, Waltrop (DE)

(73) Assignees: GASCONTEC GMBH, Bad Homburg (DE); THYSSENKRUPP UHDE GMBH, Dortmund (DE)

( * ) Notice: Subject to any disclaimer, the term of this patent is extended or adjusted under 35 U.S.C. 154(b) by 610 days.

(21) Appl. No.: 17/604,665

(22) PCT Filed: Apr. 8, 2020

(86) PCT No.: PCT/EP2020/060018
§ 371 (c)(1),
(2) Date: Oct. 18, 2021

(87) PCT Pub. No.: WO2020/212222
PCT Pub. Date: Oct. 22, 2020

(65) Prior Publication Data
US 2022/0251010 A1    Aug. 11, 2022

(30) Foreign Application Priority Data

Apr. 18, 2019  (DE) ...................... 10 2019 110 392.4
Jun. 18, 2019  (EP) ..................................... 19180879

(51) Int. Cl.
*C07C 29/152*    (2006.01)
*B01J 19/24*     (2006.01)
(Continued)

(52) U.S. Cl.
CPC ............ *C07C 29/152* (2013.01); *B01J 19/245* (2013.01); *B01J 19/2465* (2013.01); *C01B 3/36* (2013.01);
(Continued)

(58) Field of Classification Search
None
See application file for complete search history.

(56) References Cited

U.S. PATENT DOCUMENTS 6,881,758 B2    4/2005  Guillard et al.
2021/0130272 A1*  5/2021  Lepri .................... C07C 31/04

FOREIGN PATENT DOCUMENTS

| CA | 3013967 A1 * | 8/2017 | ............ B01J 8/0457 |
| EP | 2011564 A1 | 1/2009 | |
| WO | 2005108336 A1 | 11/2005 | |

OTHER PUBLICATIONS

International Search Report issued Jul. 22, 2020 re: Application No. PCT/EP2020/060018, pp. 1-2, citing: EP 2011564 A1 and WO 2005/108336 A1.

* cited by examiner

Primary Examiner — Medhanit W Bahta
(74) Attorney, Agent, or Firm — CANTOR COLBURN LLP

(57) ABSTRACT

A method for synthesizing methanol, wherein a fuel stream containing carbon is supplied to a synthesis gas reactor arrangement to obtain a synthesis gas stream including hydrogen and carbon oxides that is supplied to a first reactor stage of a methanol reactor arrangement for partial conversion into methanol, and is obtained with a generation pressure higher than the synthesis pressure with which the synthesis gas stream is partially converted into methanol. A residue gas stream is obtained from the methanol reactor arrangement, supplied to a recycle compressor and to the (Continued)

methanol reactor arrangement. Before being supplied to the first reactor stage, the synthesis gas stream is supplied to a heat recovery device to recover heat. A recovery stream is supplied to a hydrogen recovery arrangement to obtain an H-recycle stream. The pressure of the unreacted hydrogen is increased before it is supplied again to the first reactor stage.

15 Claims, 5 Drawing Sheets

(51) Int. Cl.
    *C01B 3/36*     (2006.01)
    *C07C 29/151*     (2006.01)

(52) U.S. Cl.
    CPC .. *C07C 29/1518* (2013.01); *C01B 2203/0244* (2013.01); *C01B 2203/025* (2013.01); *C01B 2203/042* (2013.01); *C01B 2203/061* (2013.01); *C01B 2203/148* (2013.01)

METHOD AND SYSTEM FOR THE SYNTHESIS OF METHANOL

TECHNICAL FIELD

The disclosure relates to a method for the synthesis of methanol according to the preamble of claim 1 and a system for the synthesis of methanol according to the preamble of claim 15.

BACKGROUND

Methanol is produced regularly in a reactor of a system for the synthesis of methanol, to which reactor a synthesis gas stream comprising hydrogen and carbon oxides is supplied and in which the exothermic reaction for the production of methanol takes place.

In principle, it is advisable to carry out the methanol synthesis at high pressure. Therefore, a synthesis gas compressor is regularly provided in the system, said compressor compressing the synthesis gas stream to the desired pressure. However, such a synthesis gas compressor is particularly energy-intensive and therefore a significant cost factor in the synthesis of methanol.

There are approaches to dispense with such a synthesis gas compressor in the prior art. The American patent U.S. Pat. No. 6,881,758 B2 describes a system for the synthesis of methanol which does not require a synthesis gas compressor. Specifically, the synthesis gas is already provided in the corresponding reactor with the addition of pressure-increased oxygen, for example, by autothermal reforming, at a pressure of 60 bar, so that the synthesis gas can be supplied to the methanol synthesis reactor without increasing the pressure.

A disadvantage of this prior art is that when the synthesis gas is generated by autothermal reforming, the stoichiometry preferred for methanol synthesis cannot be achieved.

The patent application WO 2005/108336 A1 from the prior art also describes a system for the synthesis of methanol, in which no synthesis gas compressor is provided either. In the system shown in WO 2005/108336 A1, the synthesis gas is obtained by non-catalytic partial oxidation. It is true that hydrogen which was obtained by a PSA from a residue gas of the methanol reactor is recycled to this methanol reactor, said hydrogen being either not compressed at all or being compressed using its own compressor. However, on the one hand, the compression of a pure hydrogen stream is complex, and, on the other hand, the provision of a further compressor is costly.

EP 2 011 564 A1 from the prior art, on which the present disclosure is based, provides both the omission of a synthesis gas compressor and the measure that a hydrogen stream, which was obtained from unreacted residue gas by means of a PSA, is supplied back to the recycle compressor. A disadvantage of the solution shown here, however, is that the stream supplied to the PSA has already experienced a pressure increase by the recycle compressor. The fact that the return from the output of the recycle compressor to the input of the recycle compressor thus takes place in a separate cycle, a dimensioning of the recycle compressor is required, which is larger than would be necessary per se.

SUMMARY

Based on this prior art, the disclosure therefore improves and further develops the method known from the prior art for the synthesis of methanol without a synthesis gas compressor and the system known from the prior art for the synthesis of methanol without a synthesis gas compressor, furthermore that no separate compressor is required for the hydrogen to be returned and that the recycle compressor can be dimensioned smaller.

In relation to a method for the synthesis of methanol according to the preamble of claim 1, this is achieved by the features of the characterizing part of claim 1. In relation to a system for the synthesis of methanol according to the preamble of claim 15, this is achieved by the features of the characterizing part of claim 15.

The disclosure is based on the knowledge that the extracted hydrogen from the hydrogen recovery can be conducted in such a way that it experiences a pressure increase exactly once by the recycle compressor between emerging from the first reactor stage of the methanol synthesis and being supplied again to the first reactor stage of the methanol synthesis. This prevents a repeated and thus basically unnecessary increase in pressure of the hydrogen. The dimensions of the recycle compressor can then be reduced as a result.

The proposed method is used for the synthesis of methanol. In the proposed method, a fuel stream containing carbon is supplied to a synthesis gas reactor arrangement for obtaining a synthesis gas stream comprising hydrogen and carbon oxides. The synthesis gas stream thus comprises hydrogen, carbon monoxide and carbon dioxide and can particularly also contain other components such as nitrogen and noble gases. The synthesis gas stream can also be referred to as the fresh gas stream.

Likewise, in the method according to the proposal, the synthesis gas stream is supplied to a first reactor stage of a methanol reactor arrangement for partial conversion into methanol. The feature of the partial conversion into methanol is based on the fact that an unconverted residue of starting materials emerges from the methanol reactor arrangement and therefore the conversion does not take place completely. The methanol reactor arrangement can have several reactor stages or only a single reactor stage. If the methanol reactor arrangement has only a single reactor stage, the first reactor stage is this single reactor stage of the methanol reactor arrangement. The first reactor stage of the methanol reactor arrangement is that reactor stage of the methanol reactor arrangement to which the synthesis gas stream is supplied before it or a remaining residue gas stream is supplied to a further reactor stage. In this respect, the first reactor stage is the reactor stage of the methanol reactor arrangement that is positioned first in terms of process technology. This fact coincides with the possible designation of the synthesis gas stream as a fresh gas stream. Each individual reactor stage of the methanol reactor arrangement can have a plurality of individual reactors for the methanol synthesis that are connected in parallel with one another in terms of process technology.

According to the proposed method, the synthesis gas stream is obtained in the synthesis gas reactor arrangement with a generation pressure that is higher than the synthesis pressure with which the synthesis gas stream in the first reactor stage is partially converted into methanol. In other words, the synthesis gas stream, and thus the synthesis gas, does not experience any pressure increase from the time it is generated until it reaches the methanol reactor arrangement for the methanol synthesis. Particularly, there is no pressure increase of the synthesis gas stream after it has been generated by a compressor which is upstream of the methanol synthesis and thus downstream of the synthesis gas production. It can also be the case that residue gas remaining after passing through the methanol reactor arrangement experiences an increase in pressure. This is explained below.

The proposed method provides that a residue gas stream comprising unreacted carbon oxides is obtained from the methanol reactor arrangement, said residue gas stream being supplied to a recycle compressor to increase the pressure of the residue gas stream. The residue gas stream also comprises unreacted hydrogen. If the methanol reactor arrangement has more than one reactor stage, this residue gas stream can be obtained after any reactor stage.

The proposed method further provides that the pressure-increased residue gas stream is supplied to the methanol reactor arrangement for partial conversion into methanol. It is a matter of returning the now pressure-increased residue gas stream to the methanol reactor arrangement from which the residue gas stream was obtained.

The proposed method also provides that, before being supplied to the first reactor stage, the synthesis gas stream is supplied to a heat recovery device for recovering heat from the synthesis gas stream. In other words, in terms of process technology, this heat recovery device is arranged between the synthesis gas reactor arrangement and the methanol reactor arrangement. It should be noted here that the heat recovery device usually only represents one stage of a heat recovery arrangement having a plurality of heat recovery devices. In other words, it can be the case that the synthesis gas stream is supplied to only one heat recovery device from a plurality of interconnected heat recovery devices before being supplied to the methanol reactor arrangement.

The proposed method additionally provides that a recovery stream with unreacted hydrogen from an unreacted residue gas of the first reactor stage is supplied to a hydrogen recovery arrangement for obtaining an H-recycle stream containing the unreacted hydrogen of the recovery stream. The result is that the hydrogen of the H-recycle stream corresponds at least partially and preferably completely to the unreacted hydrogen of the recovery stream. The unreacted residue gas may only be part of the total unreacted gas from the first reactor stage. It can also be the case that the unreacted hydrogen is only part of the total unreacted hydrogen in the first reactor stage.

The proposed method provides that this unreacted hydrogen of the recovery stream is supplied again to the first reactor stage for at least partial conversion into methanol. The unreacted hydrogen of the recovery stream can be supplied again to the first reactor stage either directly or indirectly. In the case of indirect supply, the unreacted hydrogen is first supplied to other devices.

The proposed method is characterized in that the pressure of unreacted hydrogen of the recovery stream is increased exactly once by the recycle compressor with the unreacted carbon oxides from the first reactor stage before it is supplied again to the first reactor stage. In other words, a pressure increase takes place only once, specifically by the recycle compressor, between the emerging of the unreacted hydrogen from the first reactor stage and said unreacted hydrogen being supplied again to the first reactor stage. Since the recycle compressor, as already stated, increases the pressure of the residue gas stream comprising unreacted carbon oxides, the recycle compressor increases the pressure with the unreacted carbon oxides. Likewise, unreacted hydrogen from the first reactor stage, which was not supplied to the hydrogen recovery arrangement, is increased in pressure by the recycle compressor.

Repeated pressure increases that are unnecessary in themselves are thus avoided. It should be noted that this requirement of the exactly one-time pressure increase by the recycle compressor only affects the unreacted hydrogen from the first reactor stage, which is also contained in the recovery stream. If there is, as is regularly the case, unreacted hydrogen from the first reactor stage which is not contained in the recovery stream, it is not necessary for this unreacted hydrogen to also experience exactly one pressure increase by the recycle compressor outside the recovery stream. Rather, both multiple increases in pressure and no increase in pressure at all are then possible.

As described below, this supplying of the unreacted hydrogen again to the first reactor stage can take place indirectly such that the hydrogen is supplied to the methanol reactor arrangement as part of a series of further streams.

In principle, the above pressure increase of the unreacted hydrogen can be a pressure increase by any amount. It is preferred that the unreacted hydrogen, before the at least partial conversion into methanol, is increased to a pressure that is higher than the pressure of the H-recycle stream from the hydrogen recovery arrangement. It can also be the case that the unreacted hydrogen is increased to a pressure that is higher than the pressure of the recovery stream when it is supplied to the hydrogen recovery arrangement, before it is supplied again into the first reactor stage.

The pressure increase of the unreacted hydrogen can, on the one hand, take place before it is supplied to the hydrogen recovery arrangement. It is possible that the pressure of the recovery stream is increased overall. The pressure increase of the unreacted hydrogen can, however, also take place after it has been supplied to the hydrogen recovery arrangement. Therefore, the pressure of the unreacted hydrogen of the H-recycle stream can be increased by increasing the pressure of the H-recycle stream overall.

The synthesis gas reactor arrangement, the methanol reactor arrangement, the heat recovery device, the recycle compressor and the hydrogen recovery arrangement can be comprised by a system for the synthesis of methanol.

The generation pressure is preferably more than 60 bar or more than 70 bar or more than 80 bar. The generation pressure can also be more than 90 bar and particularly more than 100 bar.

In principle, the residue gas stream supplied to the recycle compressor can have any composition as long as the residue gas stream comprises unreacted carbon oxides in any proportion and the unreacted hydrogen of the recovery stream. However, it is preferred that the residue gas stream supplied to the recycle compressor has a molar hydrogen content of less than 90%, particularly less than 85% and further particularly less than 80%. Alternatively or additionally, it is possible for the residue gas stream supplied to the recycle compressor to have a molar hydrogen content of greater than 50%, particularly greater than 60% and further particularly greater than 70%. This molar proportion of hydrogen relates to the total molar proportion of hydrogen of the residue gas stream. Therefore, this not only includes the hydrogen from the recovery stream, but also other hydrogen in the residue gas stream.

The methanol reactor arrangement preferably comprises a methanol separation device for obtaining the unreacted residue gas of the first reactor stage and a crude methanol stream of the first reactor stage. In principle, the methanol separation device can function in any way. Particularly, it is possible for the methanol separation device to comprise a condensation device for obtaining the unreacted residue gas of the first reactor stage and the crude methanol stream of the first reactor stage by condensation.

It may be that only part of the pressure-increased residue gas stream is supplied to the methanol reactor arrangement.

Particularly, it is preferred that part of the pressure-increased residue gas stream is branched off and supplied to the synthesis gas reactor arrangement. Particularly, it can be provided that the branched off part of the pressure-increased residue gas stream is supplied to the fuel stream.

As already stated, it is possible for the methanol reactor arrangement to comprise only a single methanol reactor stage. A further preferred embodiment of the method is characterized in that the methanol reactor arrangement has a plurality of reactor stages for methanol synthesis which are connected in series in terms of process technology. Each individual reactor stage can have one or more reactors. The reactors of a reactor stage can particularly be arranged in parallel with one another in terms of process technology. It can furthermore be that a respective unreacted residue gas is obtained from each of the plurality of reactor stages by the methanol separation device.

The fact that the reactor stages are connected in series in terms of process technology means that residue gas from one reactor stage, provided it is not the last reactor stage in the series of reactor stages, is supplied directly or indirectly to each subsequent reactor stage. In principle, the above recycle compressor can be arranged as desired with regard to the plurality of reactor stages. One variant is that the recycle compressor is arranged between two reactor stages in terms of process technology. This means that at least part of the unreacted residue gas from a reactor stage is supplied to the recycle compressor as a residue gas stream and the pressure-increased residue gas stream is then supplied to the reactor stage downstream of this reactor stage.

In principle, the H-recycle stream can be directed as desired, as long as at least part of its hydrogen is converted into methanol. According to a further preferred embodiment of the method, it is preferred in this regard that the H-recycle stream is supplied to the unreacted residue gas in a reactor stage downstream of the first reactor stage in terms of process technology. In other words, the unreacted hydrogen of the H-recycle stream is treated together with at least part of the unreacted residue gas from a reactor stage other than the first reactor stage after being supplied.

It is preferred that the H-recycle stream is supplied to the recycle compressor to increase the pressure with the residue gas stream.

According to a preferred embodiment of the method, it is provided that the residue gas stream is obtained from a reactor stage which is downstream of the first reactor stage in terms of process technology. In other words, the residue gas stream supplied to the recycle compressor does not come from the first reactor stage, that is, the reactor stage to which the synthesis gas stream is supplied directly, but from a downstream reactor stage. It can also be that the recycle compressor supplies the pressure-increased residue gas stream to the first reactor stage. In principle, however, the pressure-increased residue gas stream can also be supplied to another reactor stage of the plurality of reactor stages.

A further preferred embodiment of the proposed method is characterized in that the residue gas stream is obtained from a reactor stage of the plurality of reactor stages which is positioned last in terms of process technology.

In principle, the recovery stream can be obtained at any point and from any source within the methanol reactor arrangement. All that is required is that it contains unreacted hydrogen from an unreacted residue gas from the first reactor stage. A first preferred variant provides that the recovery stream is at least partially branched off from the unreacted residue gas from the first reactor stage. It may be that the recovery stream is at least partially branched off upstream of the recycle compressor in terms of process technology.

However, it can also be that the recovery stream has already experienced a pressure increase by the recycle compressor. A further preferred embodiment of the method is therefore characterized in that the recovery stream is supplied to the hydrogen recovery arrangement with a supply pressure that is higher than a residue gas pressure with which the residue gas stream is obtained from the methanol reactor arrangement. A preferred option for increasing the pressure of the recovery stream is to have this recovery stream previously compressed by the recycle compressor. Accordingly, it is preferred that the recovery stream is branched off from the residue gas stream downstream of the recycle compressor in terms of process technology.

However, it can also be that the hydrogen recovery arrangement is supplied with more than one stream from which hydrogen is obtained. According to a preferred embodiment of the method, it is provided that at least part of the synthesis gas stream is branched off for supply to a water-gas shift reaction device. It is also possible for the synthesis gas stream as a whole to be supplied to the water-gas shift reaction device. It is also preferred that a further recovery stream is at least partially obtained from the water-gas shift reaction device and supplied to the hydrogen recovery arrangement for obtaining the H-recycle stream. In other words, at least part of the hydrogen of the H-recycle stream is obtained from this further recovery stream. This water-gas shift reaction device can be comprised in the system for the synthesis of methanol.

Particularly, at least part of the carbon oxide in the synthesis gas stream can react to form carbon dioxide and hydrogen in the water-gas shift reaction device by means of a water-gas shift reaction. The stoichiometry for the methanol synthesis can be improved by increasing the hydrogen content.

It can also be the case that the H-recycle stream is initially not supplied to the first reactor stage. According to a further preferred embodiment of the method, it is then provided that the H-recycle stream is supplied to the synthesis gas stream. Specifically, this means that the H-recycle stream is supplied downstream of the synthesis gas stream of the synthesis gas reactor arrangement in terms of process technology. In other words, the H-recycle stream is supplied upstream to the synthesis gas stream of the first reactor stage in terms of process technology. By supplying the synthesis gas stream to the first reactor stage of the methanol reactor arrangement, however, the hydrogen of the H-recycle stream is ultimately supplied back to the first reactor stage.

The synthesis gas reactor arrangement can have further devices in addition to a reactor for generating the synthesis gas. The synthesis gas reactor arrangement can thus have a device upstream of the reactor in terms of process technology for desulfurization of the fuel stream containing carbon, a saturation stage for saturating the fuel stream containing carbon with water, a pre-reformer for pre-reforming the fuel stream containing carbon and/or a device for heating the fuel stream containing carbon.

In principle, the synthesis gas stream can be obtained for the fuel stream in any desired manner. It is preferred that an oxygen-containing stream is supplied to the synthesis gas reactor arrangement for obtaining the synthesis gas stream. In principle, the oxygen-containing stream can also comprise further constituents in addition to the oxygen. The oxygen-containing stream can also be ambient air.

In principle, the synthesis gas stream can be obtained, for example, by steam reforming the fuel stream containing carbon. A further preferred embodiment of the method is characterized in that in the synthesis gas reactor arrangement, the synthesis gas stream is obtained from the fuel stream containing carbon by autothermal reforming. In such an autothermal reforming, a catalytic partial oxidation provides the heat required for the endothermic reforming reactions. Compared to pure steam reforming, autothermal reforming offers the advantage that the synthesis gas stream can be provided at a higher pressure. Alternatively or additionally, it is possible for the synthesis gas stream to be obtained from the fuel stream containing carbon by partial oxidation in the synthesis gas reactor arrangement.

In principle, autothermal reforming can also be operated with ambient air. However, it is preferred that the oxygen-containing stream is obtained from an air separation device for obtaining an oxygen stream from ambient air. The air separation device can furthermore also be set up to obtain a nitrogen stream. Particularly, it can then be that the oxygen-containing stream consists essentially of oxygen. The proportion of inert gases in the methanol synthesis is reduced in this way, so that various devices of the system can be dimensioned smaller.

According to a preferred embodiment of the method, it is provided that the H-recycle stream is supplied to the fuel stream. Particularly, it is possible for the H-recycle stream to be supplied to the fuel stream upstream of the synthesis gas reactor arrangement in terms of process technology.

In addition to the H-recycle stream, the hydrogen recovery arrangement can also output further streams. The hydrogen recovery arrangement preferably outputs a purge stream. Said purge stream can particularly be discharged for combustion.

In principle, the H-recycle stream can have any composition as long as it contains unreacted hydrogen. According to a further preferred embodiment of the method, it is provided that the H-recycle stream has a higher molar proportion of hydrogen than the recovery stream. In other words, the hydrogen in the H-recycle stream is enriched with respect to the recovery stream. It is also preferred that the H-recycle stream comprises a higher molar proportion of hydrogen than the purge stream.

In principle, the hydrogen recovery arrangement can function according to any desired principle, for example, based on a membrane or a refrigeration device. A preferred embodiment of the method is characterized in that the hydrogen recovery arrangement has a pressure swing adsorption device (PSA) for obtaining the H-recycle stream from the recovery stream. A high level of hydrogen recovery can be achieved in the H-recycle stream in this way. Likewise, the pressure losses in such a pressure swing adsorption device are still acceptable. High hydrogen purity is fundamentally not required in the present case, but can be achieved. It is therefore possible for the H-recycle stream to consist essentially of hydrogen.

The proposed system is used for the synthesis of methanol. It has a synthesis gas reactor arrangement for obtaining a synthesis gas stream comprising hydrogen and carbon oxides from a fuel stream containing carbon, a methanol reactor arrangement having a first reactor stage, a heat recovery device for recovering heat from the synthesis gas stream, a hydrogen recovery arrangement and a recycle compressor.

In the proposed system, the synthesis gas stream is supplied to the first reactor stage for partial conversion into methanol and obtained in the synthesis gas reactor arrangement with a generation pressure that is higher than the synthesis pressure with which the synthesis gas stream in the first reactor stage is partially converted into methanol.

Furthermore, in the proposed system, a residue gas stream comprising unreacted carbon oxides is obtained from the methanol reactor arrangement, said residue gas stream being supplied to the recycle compressor to increase the pressure of the residue gas stream, wherein the pressure-increased residue gas stream is supplied to the methanol reactor arrangement for partial conversion into methanol, wherein before being supplied to the first reactor stage, the synthesis gas stream is supplied to the heat recovery device, wherein the hydrogen recovery device is supplied a recovery stream with unreacted hydrogen from an unreacted residue gas of the first reactor stage for obtaining an H-recycle stream containing the unreacted hydrogen of the recovery stream, said unreacted hydrogen of the recovery stream being supplied again to the first reactor stage for at least partial conversion into methanol.

The proposed method is characterized in that the pressure of the unreacted hydrogen of the recovery stream is increased exactly once by the recycle compressor with the unreacted carbon oxides from the first reactor stage before is supplied back to the first reactor stage.

Features, advantages and properties of the proposed system correspond to the features, advantages and properties of the proposed method and vice versa.

BRIEF DESCRIPTION OF THE DRAWINGS

Further details, features, objectives and advantages of the present disclosure are explained below with reference to the drawing, which shows only embodiments. The drawing shows FIG. 1 schematically the flow diagram of a system for carrying out the proposed method according to a first embodiment, FIG. 2 schematically the flow diagram of a system for carrying out the proposed method according to a second embodiment, FIG. 3 schematically the flow diagram of a system for carrying out the proposed method according to a third embodiment, FIG. 4 schematically the flow diagram of a system for carrying out the proposed method according to a fourth embodiment and FIG. 5 schematically the flow diagram of a system for carrying out the proposed method according to a fifth embodiment.

DETAILED DESCRIPTION OF THE DRAWINGS

Figure 1:
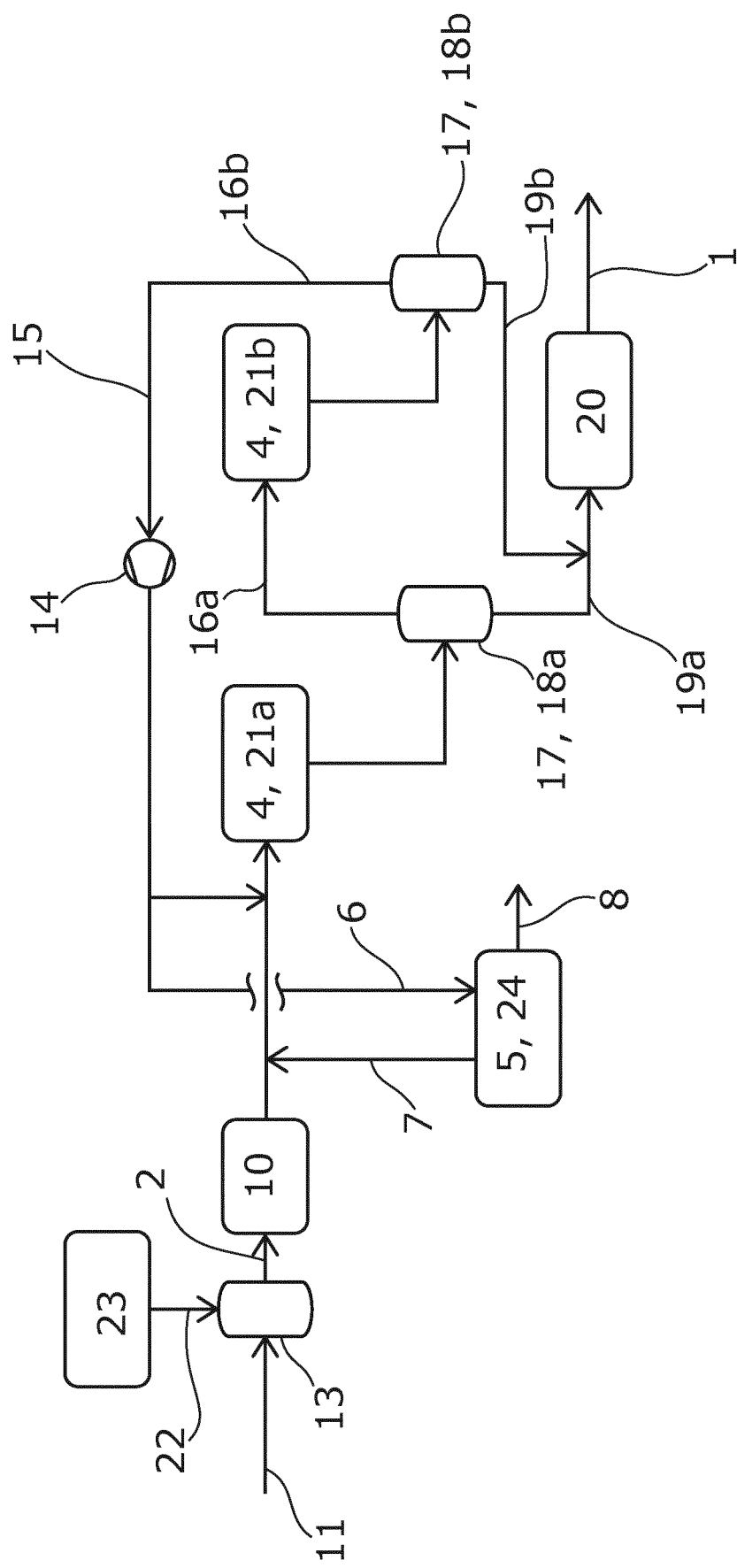

The system shown in FIG. 1 according to a first embodiment of the proposed system is used for the synthesis of methanol 1 and can be operated according to the proposed method.

A synthesis gas stream 2 consisting essentially of hydrogen, carbon monoxide and carbon dioxide is obtained from a fuel stream 11 formed by natural gas and thus contains carbon, said fuel stream being supplied to a synthesis gas reactor arrangement 13. An autothermal reforming takes place in the synthesis gas reactor arrangement 13 in order to obtain the synthesis gas stream 2. An oxygen-containing stream 22 is supplied for the autothermal reforming, said oxygen-containing stream 22 having been obtained here from an air separation device 23 and consisting essentially of oxygen. The air separation device 23 is set up to obtain an oxygen stream, here in this case, the oxygen-containing stream 22, from the ambient air. The synthesis gas stream 2 is obtained using a generation pressure of essentially 80 bar.

The synthesis gas stream 2 is first supplied to a heat recovery device, in which the synthesis gas stream 2 is cooled and part of the heat generated in the autothermal reforming is recovered in this way. The synthesis gas stream 2 of the first reactor stage 21a is then supplied to a methanol reactor arrangement 4, in which first reactor stage 21a a methanol synthesis takes place and at least part of the synthesis gas stream 2 is converted into methanol 1. The methanol synthesis takes place at a synthesis pressure of over 70 bar. A synthesis gas compressor for increasing the pressure of the synthesis gas stream 2 is therefore unnecessary.

The system has a pressure swing adsorption system 24, which can also be referred to as a PSA, designed hydrogen recovery arrangement 5, which obtains an H-recycle stream 7 from a recovery stream 6, which H-recycle stream 7 consists essentially of hydrogen. Likewise, the remaining gas is output from the hydrogen recovery arrangement 5 as a purge stream 8 and then burned in a fired heating device of the system (not shown here). The H-recycle stream 7 is supplied to the synthesis gas stream 2.

As can be seen in FIG. 1, the system of the first embodiment also has a recycle compressor 14 which compresses a residue gas stream 15. The residue gas stream 15 comprises unreacted residue gas 16b, which in turn essentially comprises those constituents of the synthesis gas which were not converted into methanol 1 in the methanol reactor arrangement 4. Correspondingly, the residue gas stream 15 comprises, particularly, unreacted carbon oxides. The residue gas stream 15, which is thus increased in pressure, is supplied to the methanol reactor arrangement 4 again for a first part.

The unreacted residue gas 16a, b is obtained from a methanol separation device 17 of the methanol reactor arrangement 4, which here comprises two condensation devices 18a, b. The unreacted residue gas 16a, b, on the one hand, and a respective crude methanol stream 19a, b on the other hand, are obtained in each of these by condensation. The crude methanol streams 19a, b are then supplied to a distillation of the system, so that the methanol 1 can be obtained from the crude methanol streams 19a, b.

In the system of the embodiment of FIG. 1, the methanol reactor arrangement 4 has two reactor stages 21a, b connected in series in terms of process technology for the synthesis of methanol. In this embodiment, the first reactor stage 21a has two isothermal reactors arranged parallel to one another and the second reactor stage 21b has a single isothermal reactor. The product stream from a respective reactor stage 21a, b is supplied to each of the two condensation devices 18a, b. That reactor stage 21a to which the synthesis gas stream 2 is supplied directly is referred to as the first reactor stage 21a. The reactor stage 21b is then downstream of first reactor stage 21a in terms of process technology in that the unreacted residue gas 16a from the first reactor stage 21a is supplied thereto for conversion into methanol 1.

In this embodiment of FIG. 1, the recovery stream 6 is branched off from the residue gas stream 15, the pressure of which has been increased by the recycle compressor. This residue gas stream 15 supplied to the recycle compressor 14 is not obtained from the unreacted residue gas 16a of the first reactor stage 21a, but from the unreacted residue gas 16b of the reactor stage downstream of the first reactor stage 21a in terms of process technology and thus the second reactor stage 21b.

Nonetheless, this residue gas stream 15 also comprises, in addition to the unreacted carbon oxides already mentioned, unreacted hydrogen from the first reactor stage 21a. Any unreacted hydrogen from the residue gas 16a of the first reactor stage 21a is supplied to the second reactor stage 21b. Since there is no complete reaction of the hydrogen in the second reactor stage 21b either, the unreacted residue gas 16b from the second reactor stage 21b also contains unreacted hydrogen from the first reactor stage 21a.

Since the recovery stream 6 was branched off from the pressure-increased residue gas stream 15, the H-recycle stream 7 also contains unreacted hydrogen from the residue gas 16a of the first reactor stage 21a. Particularly, a second part of the pressure-increased residue gas stream 15 is branched off as recovery stream 6. Because the H-recycle stream 7 is supplied to the synthesis gas stream 2, the unreacted hydrogen from the residue gas 16a of the first reactor stage 21a is supplied back into the recovery stream of this first reactor stage 21 for conversion into methanol. Between leaving the first reactor stage 21a and the renewed supply to the first reactor stage 21a, however, the unreacted hydrogen from the recovery stream 6, as a constituent of the residue gas stream 15, has experienced a pressure increase by the recycle compressor 14, exactly once and together with the unreacted carbon oxides in the residue gas stream 15. The residue gas stream 15 compressed by the recycle compressor 14 is then in turn supplied directly to the first reactor stage 21a for the first part already mentioned.

Figure 2:
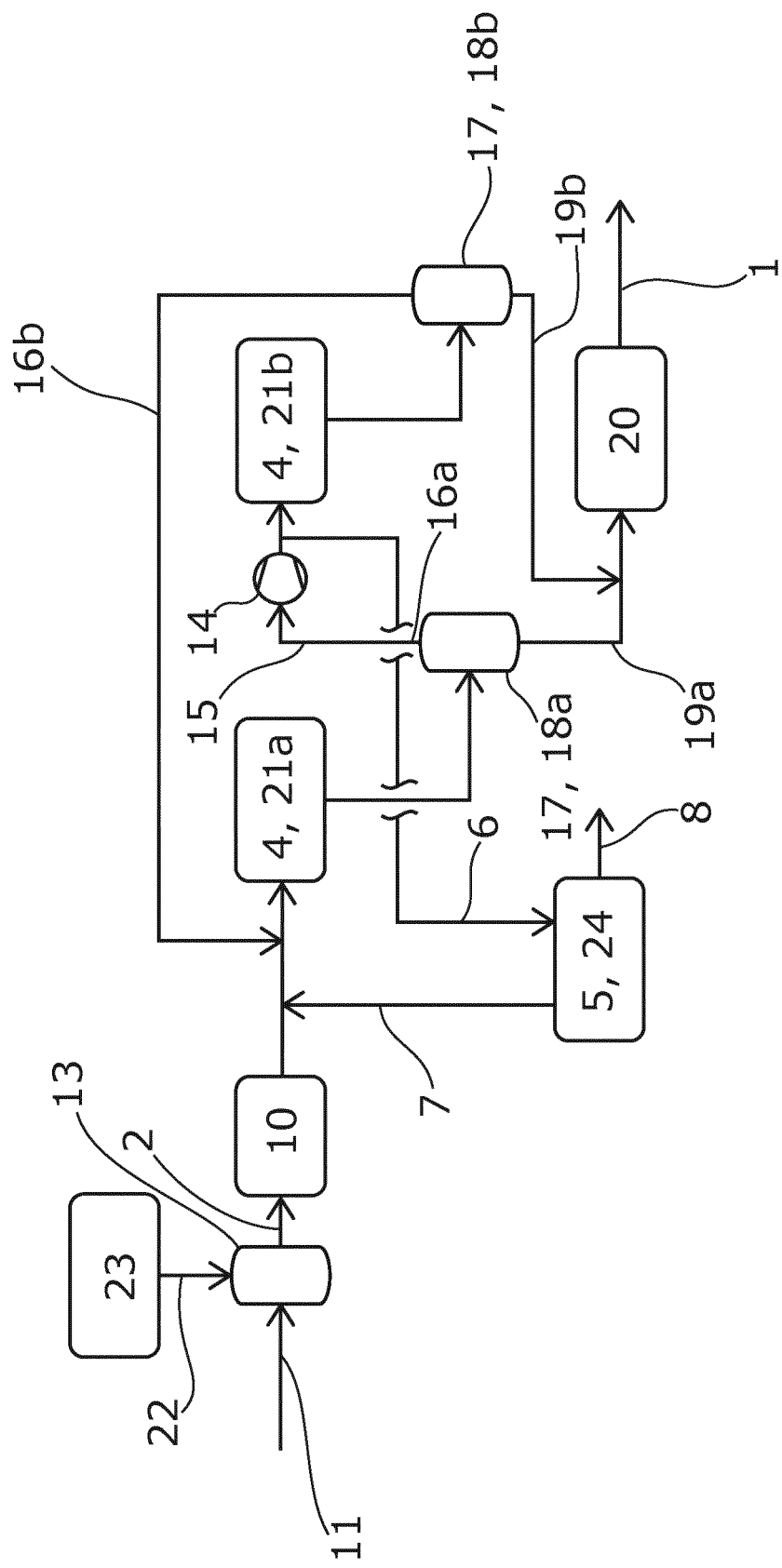

The second embodiment of the proposed system, shown in FIG. 2, differs from the embodiment in FIG. 1 in that the recycle compressor 14 is arranged in terms of process technology between the first reactor stage 21a and the reactor stage 21b downstream thereof. Consequently, the residue gas stream supplied to the recycle compressor 14 is obtained from the unreacted residue gas 16a of the first reactor stage 21a. The residue gas stream 15 comprising the unreacted carbon oxides compressed by the recycle compressor 14 is supplied to the reactor stage 21b downstream of the first reactor stage 21a. The unreacted residue gas 16b from this reactor stage 21b is supplied back to the first reactor stage 21a without further compression. In contrast to the first embodiment, the recovery stream 6 is obtained from the unreacted residue gas 16a of the first reactor stage 21a, wherein the recovery stream 6 is branched off downstream of the recycle compressor 14 in terms of process technology, likewise in accordance with the first embodiment. Consequently, in the second embodiment, too, a pressure increase by the recycle compressor 14 of the unreacted hydrogen from the residue gas 16a of the first reactor stage 21a in the recovery stream 6 containing the unreacted carbon oxides takes place exactly once, before this unreacted hydrogen is supplied back to the first reactor stage 21a.

Figure 3:
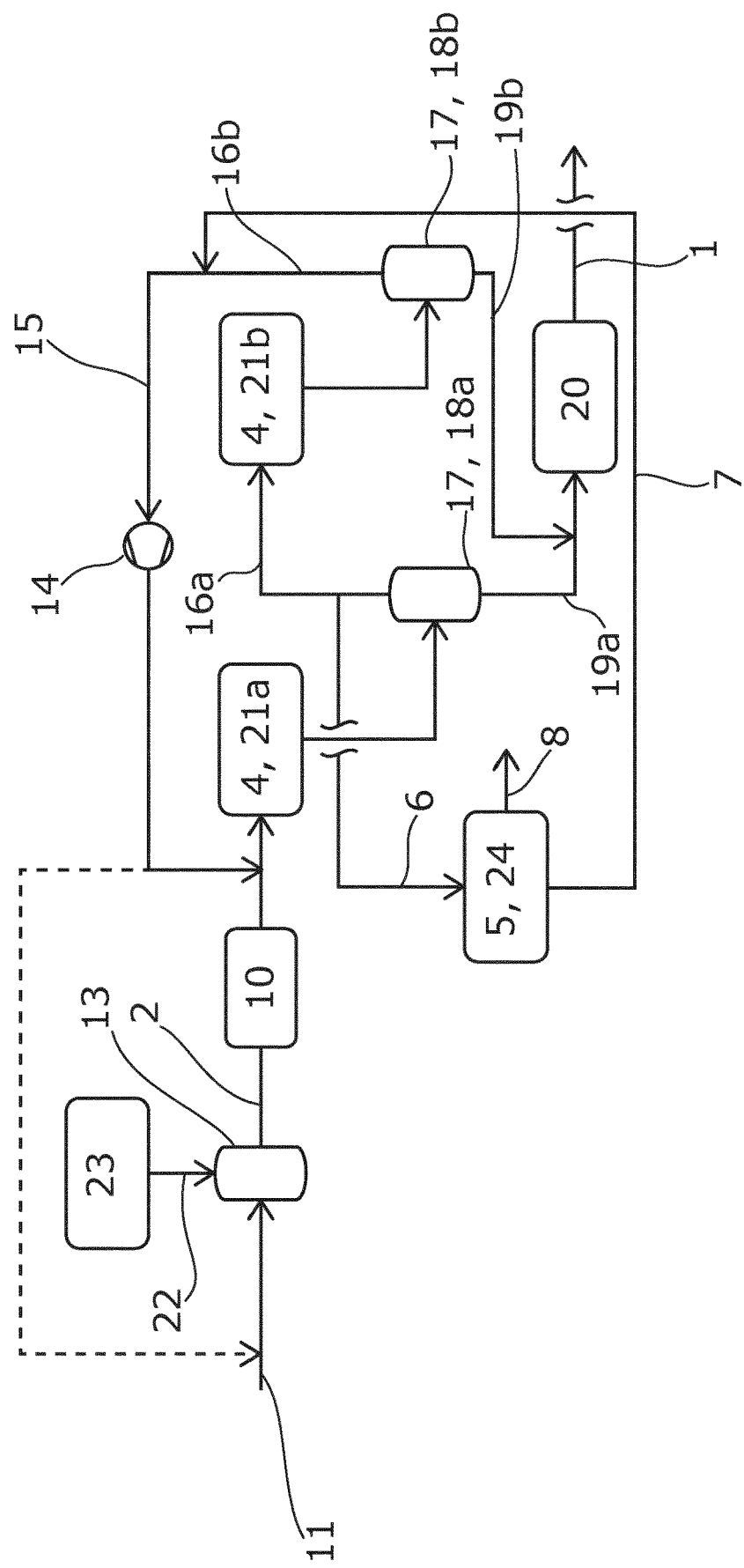

In the third embodiment of FIG. 3, the recovery stream 6 is obtained from the residue gas 16a of the first reactor stage 21a in a manner similar to that in the second embodiment. In contrast to the second embodiment, however, no recycle compressor 14 is arranged between the first reactor stage 21a and the second reactor stage 21b. Rather, as in the first embodiment, the recycle compressor 14 is arranged downstream of the second reactor stage 21b in terms of process technology.

In contrast to both the first embodiment and the second embodiment, in the third embodiment, the H-recycle stream 7 is supplied to the residue gas 16b of the second reactor stage 21b downstream of the first reactor stage 21a. Particularly, said supply takes place before the pressure increase by the recycle compressor 14. The hydrogen in the H-recycle stream 7, corresponding to the unreacted hydrogen from the residue gas 16a of the first reactor stage 21a in the recovery stream 6, receives a pressure increase by the recycle compressor 14 with the other unreacted residue gas 16b of the second reactor stage 21b and particularly with unreacted carbon oxides. This pressure increase takes place exactly once before supplying this unreacted hydrogen again to the first reactor stage 21a, which compensates for the lack of pressure increase due to the lack of a synthesis gas compressor.

In addition, it is provided in the third embodiment that part of the pressure-increased residue gas stream 15 is branched off and supplied to the fuel stream 11. However, it is also possible to dispense with this branching off of part of the pressure-increased residue gas stream 15.

Figure 4:
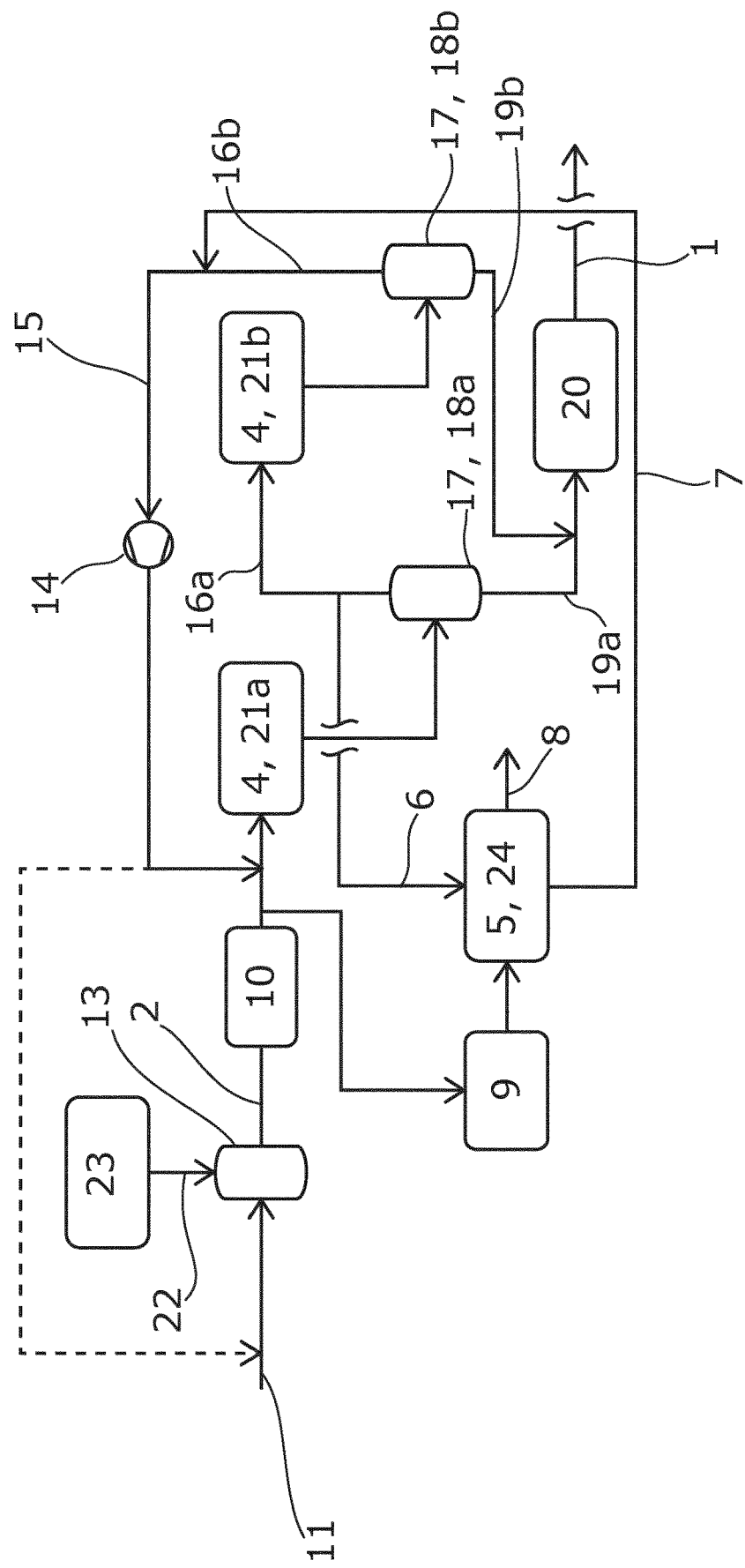

The system according to the fourth embodiment in FIG. 4 corresponds to the third embodiment in FIG. 3. However, it has a water-gas shift reaction device 9 to which part of the synthesis gas stream 2 is supplied after being supplied to the heat recovery device 10. The water-gas shift reaction taking place in the water-gas shift reaction device 9 leads to an increase in the hydrogen content in the branched-off part of the synthesis gas stream 2. The part of the synthesis gas stream 2 from the water-gas shift reaction device 9 branched off in this way and subjected to the water-gas shift reaction forms here a further recovery stream which is supplied to the hydrogen recovery arrangement 5 together with the recovery stream 6. Likewise, as in the embodiment of FIG. 3, the H-recycle stream 7 is supplied to the residue gas 16b of the second reactor stage 21b downstream of the first reactor stage 21a, so that in this embodiment, too, there is a one-time pressure increase by the recycle compressor 14 with the unreacted carbon oxides.

Figure 5:
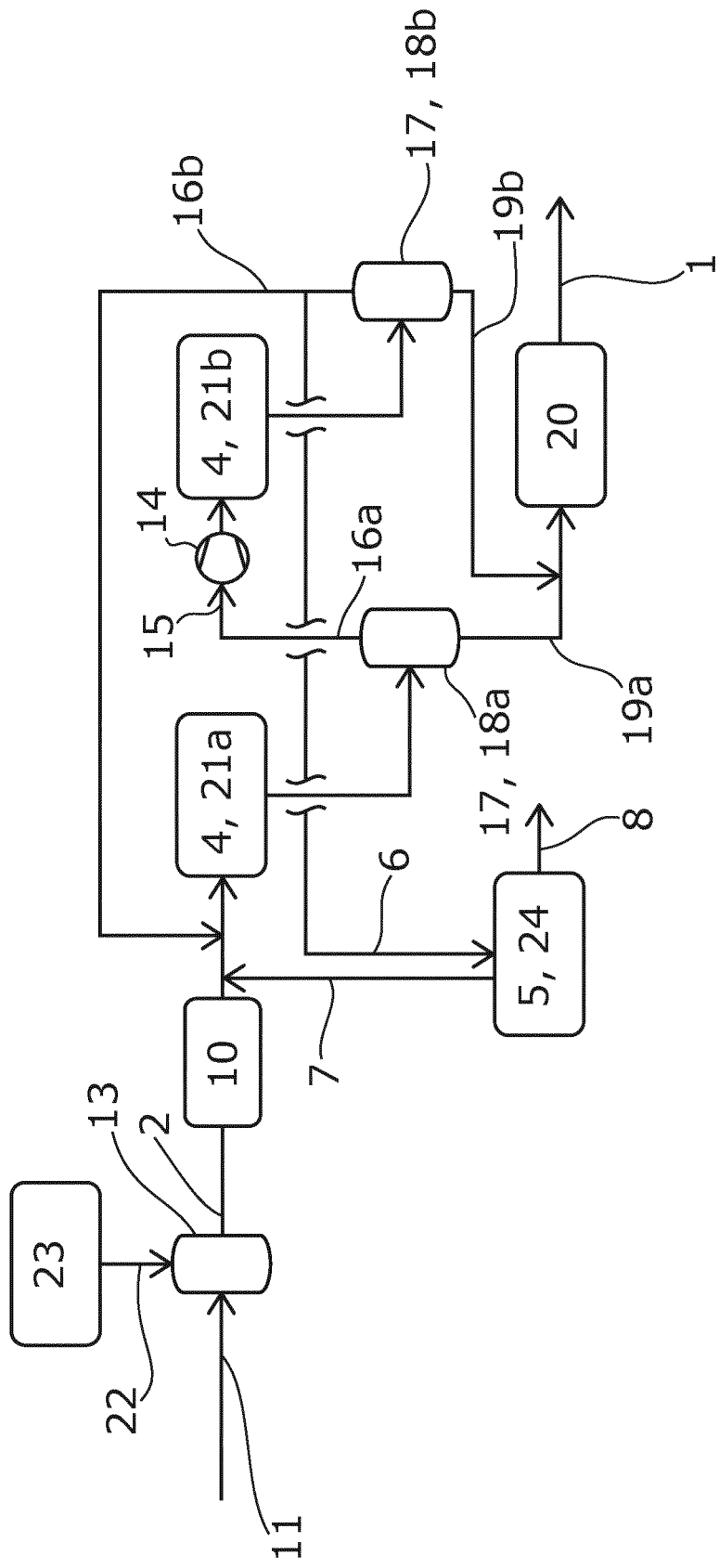

The fifth embodiment of FIG. 5 provides an arrangement of the recycle compressor 14 between the reactor stages 21a, b of the methanol reactor arrangement 4 as in the second embodiment, on which the fifth embodiment is also based. In contrast to the second embodiment, the recovery stream 6 is obtained from the residue gas 16b of the second reactor stage 21b. The hydrogen in this recovery stream 6 has experienced a pressure increase by the recycle compressor, specifically before it is supplied to the second reactor stage 21b.

The invention claimed is:

1. A method for the synthesis of methanol, the method including the following steps: a fuel stream containing carbon being supplied to a synthesis gas reactor arrangement for obtaining a synthesis gas stream comprising hydrogen and carbon oxides, the synthesis gas stream being supplied to a first reactor stage of a methanol reactor arrangement for partial conversion into methanol, the synthesis gas stream being obtained in the synthesis gas reactor arrangement with a generation pressure that is higher than the synthesis pressure with which the synthesis gas stream in the first reactor stage is partially converted into methanol, a residue gas stream comprising unreacted carbon oxides being obtained from the methanol reactor arrangement, said residue gas stream being supplied to a recycle compressor for increasing the pressure of the residue gas stream, the pressure-increased residue gas stream being supplied to the methanol reactor arrangement for partial conversion into methanol, the synthesis gas stream, before being supplied to the first reactor stage, being supplied to a heat recovery device for recovering heat from the synthesis gas stream, a recovery stream with unreacted hydrogen from an unreacted residue gas of the first reactor stage being supplied to a hydrogen recovery arrangement for obtaining an H-recycle stream containing the unreacted hydrogen from the recovery stream, said unreacted hydrogen of the recovery stream being supplied again to the first reactor stage for at least partial conversion into methanol, wherein the pressure of the unreacted hydrogen of the recovery stream is increased exactly once by the recycle compressor with the unreacted carbon oxides from the first reactor stage before it is supplied again to the first reactor stage.

2. The method according to claim 1, wherein the methanol reactor arrangement comprises a methanol separation device for obtaining the unreacted residue gas from the first reactor stage and a raw methanol stream from the first reactor stage, wherein the methanol separation device comprises a condensation device for obtaining the unreacted residue gas from the first reactor stage and the raw methanol stream from the first reactor stage by condensation.

3. The method according to claim 2, wherein part of the pressure-increased residue gas stream is branched off and supplied to the synthesis gas reactor arrangement, wherein the branched-off part of the pressure-increased residue gas stream is supplied to the fuel stream.

4. The method according to claim 1, wherein the methanol reactor arrangement has a plurality of reactor stages for methanol synthesis connected in series in terms of process technology, the recycle compressor is arranged between two reactor stages in terms of process technology, such that a respective unreacted residue gas is obtained from each of the plurality of reactor stages by the methanol separation device.

5. The method according to claim 4, wherein the H-recycle stream is supplied to the unreacted residue gas of a reactor stage downstream of the first reactor stage in terms of process technology, wherein the H-recycle stream is supplied to the recycle compressor together with the residue gas stream for increasing the pressure.

6. The method according to claim 4, wherein the residue gas stream is obtained from a reactor stage downstream of the first reactor stage in terms of process technology, wherein the recycle compressor supplies the pressure-increased residue gas stream to the first reactor stage.

7. The method according to claim 6, wherein the residue gas stream is obtained from a reactor stage of the plurality of reactor stages which is positioned last in terms of process technology.

8. The method according to claim 1, wherein the recovery stream is at least partially branched off from the unreacted residue gas of the first reactor stage, further wherein the recovery stream is at least partially branched off upstream of the recycle compressor in terms of process technology.

9. The method according to claim 8, wherein the recovery stream is supplied to the hydrogen recovery arrangement with a supply pressure that is higher than a residue gas pressure with which the residue gas stream is obtained from the methanol reactor arrangement, wherein the recovery stream is at least partially branched off from the residue gas stream downstream of the recycle compressor in terms of process technology.

10. The method according to claim 1, wherein the H-recycle stream is supplied to the synthesis gas stream.

11. The method according to claim 1, wherein, in order to obtain the synthesis gas stream, an oxygen-containing stream is supplied to the synthesis gas reactor arrangement, such that in the synthesis gas reactor arrangement, the synthesis gas stream is obtained by autothermal reforming or partial oxidation from the fuel stream containing carbon, wherein the oxygen-containing stream is obtained from an air separation device for obtaining an oxygen stream from ambient air, further that the oxygen-containing stream comprises oxygen.

12. The method according to claim 1, wherein the H-recycle stream is supplied to the fuel stream, upstream of the synthesis gas reactor arrangement in terms of process technology, and the hydrogen recovery arrangement outputs a purge stream, which is further discharged for burning.

13. The method according to claim 1, wherein the H-recycle stream has a higher molar proportion of hydrogen than the recovery stream, wherein the H-recycle stream has a higher molar proportion of hydrogen than the purge stream.

14. The method according to claim 1, wherein the hydrogen recovery arrangement has a pressure swing adsorption device for obtaining the H-recycle stream from the recovery stream, wherein the H-recycle stream comprises hydrogen.

15. A system for the synthesis of methanol having a synthesis gas reactor arrangement for obtaining a synthesis gas stream comprising hydrogen and carbon oxides from a fuel stream containing carbon, having a methanol reactor arrangement which has a first reactor stage, having a heat recovery device for recovering heat from the synthesis gas stream, having a hydrogen recovery arrangement and having a recycle compressor, the synthesis gas stream being supplied to the first reactor stage for partial conversion into methanol and being obtained in the synthesis gas reactor arrangement with a generation pressure that is higher than the synthesis pressure with which the synthesis gas stream in the first reactor stage is partially converted into methanol, a residue gas stream comprising unreacted carbon oxides being obtained from the methanol reactor arrangement, said residue gas stream being supplied to the recycle compressor to increase the pressure of the residue gas stream, the pressure-increased residue gas stream being supplied to the methanol reactor arrangement for partial conversion into methanol, the synthesis gas stream, before being supplied to the first reactor stage, being supplied to the heat recovery device, the hydrogen recovery device being supplied a recovery stream with unreacted hydrogen from an unreacted residue gas of the first reactor stage for obtaining an H-recycle stream containing the unreacted hydrogen of the recovery stream, said unreacted hydrogen of the recovery stream being supplied again to the first reactor stage for at least partial conversion into methanol, wherein the pressure of the unreacted hydrogen of the recovery stream is increased exactly once by the recycle compressor with the unreacted carbon oxides from the first reactor stage before it is supplied again to the first reactor stage.

* * * * *